United States Patent [19]

Hannam et al.

[11] Patent Number: 5,078,727
[45] Date of Patent: Jan. 7, 1992

[54] CATHETERS

[76] Inventors: Peter H. Hannam, 64, The Boulevard, Worthing, West Sussex, England; Peter Carpenter, 43, Servetus St, Swanbourne, Perth, Western Australia, Australia

[21] Appl. No.: 542,081

[22] Filed: Jun. 22, 1990

[30] Foreign Application Priority Data

Jul. 14, 1989 [GB] United Kingdom ............... 8916158

[51] Int. Cl.$^5$ ............................................. A61M 29/02
[52] U.S. Cl. ...................................... 606/194; 604/96
[58] Field of Search ............... 606/194, 192, 193, 196; 604/103, 96

[56] References Cited

U.S. PATENT DOCUMENTS

| | | |
|---|---|---|
| 4,276,874 | 7/1981 | Wolvek et al. |
| 4,323,071 | 4/1982 | Simpson et al. ......... 128/DIG. 18 X |
| 4,702,252 | 10/1987 | Brooks et al. ................. 604/103 X |
| 4,798,586 | 1/1989 | Stevens .......................... 606/194 X |
| 4,813,934 | 5/1989 | Engelson et al. |
| 4,820,349 | 4/1989 | Saab ................................. 606/194 |
| 4,943,278 | 7/1990 | Euteneuer et al. ................ 606/194 |

FOREIGN PATENT DOCUMENTS 8700442 1/1987 PCT Int'l Appl.

Primary Examiner—Michael H. Thaler
Attorney, Agent, or Firm—Pollock, Vande Sande and Priddy

[57] ABSTRACT

A balloon dilatation catheter has a flexible, hollow inner shaft and an outer, braided shaft with a balloon that is inflatable by fluid introduced between the outer and inner shaft. The inner shaft is fixed relative to the outer shaft at both ends such that, when the balloon is inflated, the outer shaft shortens and the excess length of the inner shaft is accommodated by the inner shaft bending into a coil within the balloon.

10 Claims, 2 Drawing Sheets

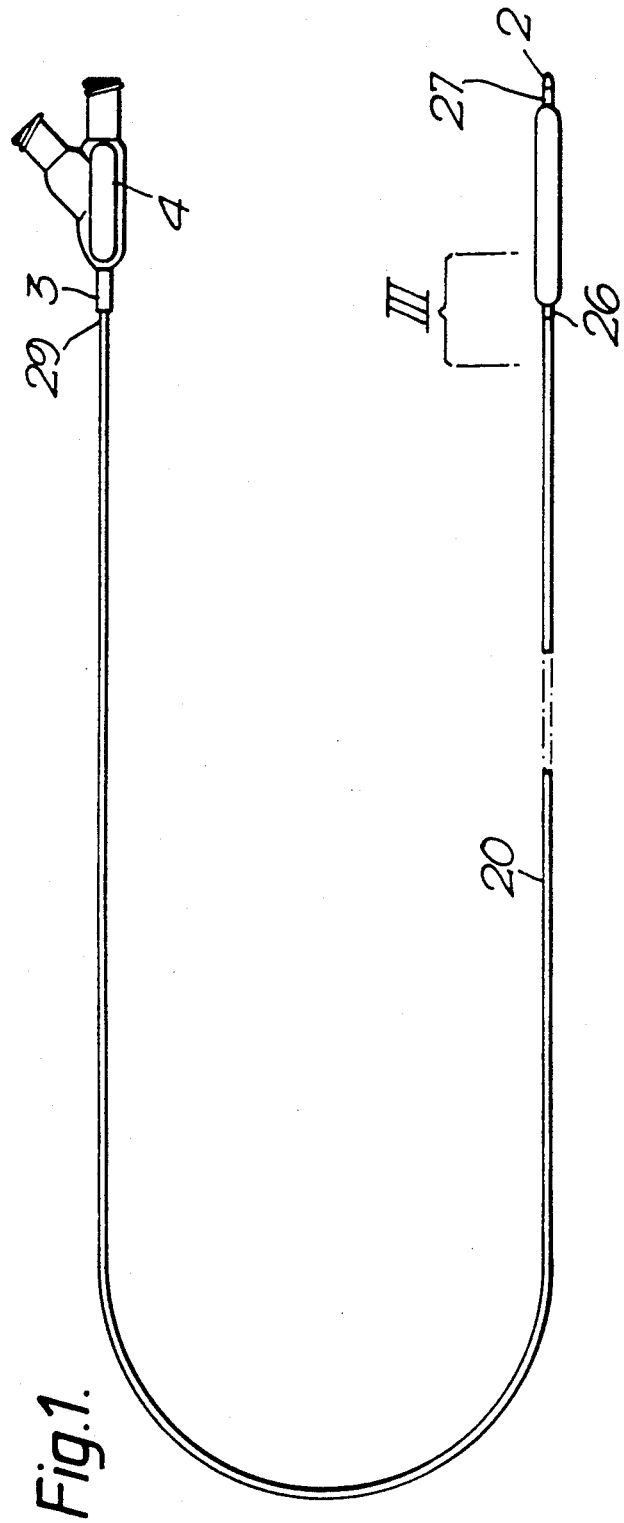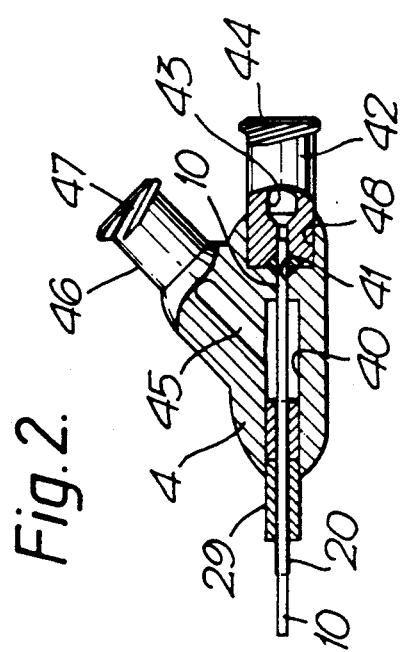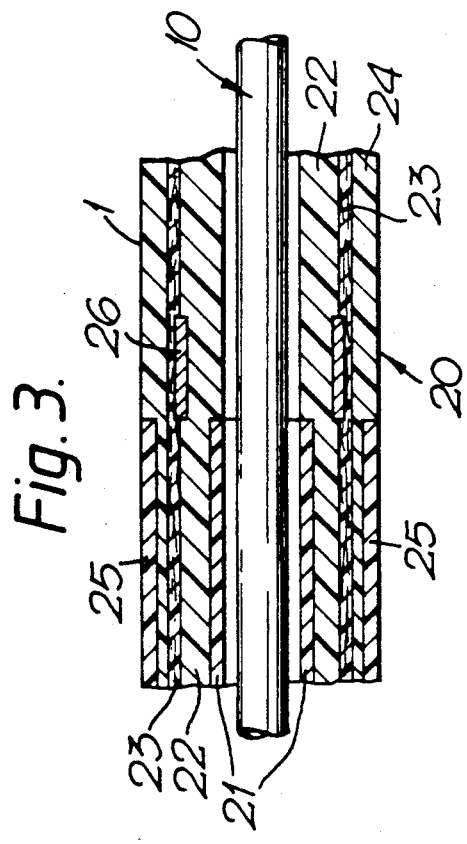

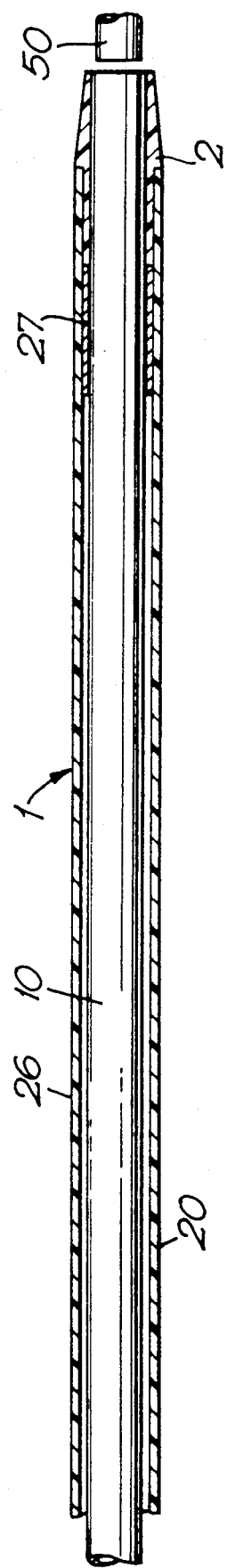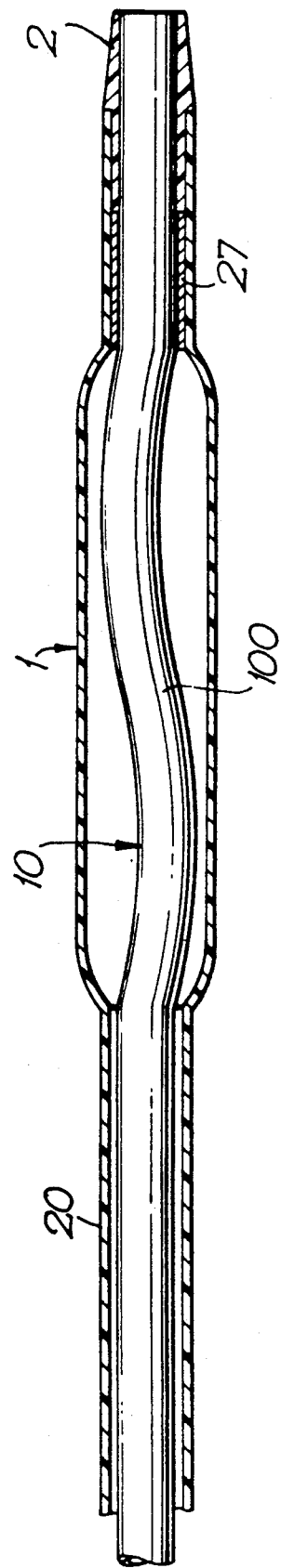

CATHETERS

BACKGROUND OF THE INVENTION

This invention relates to catheters.

The invention is more particularly concerned with balloon catheters, such as for use in angioplasty or balloon dilatation.

Balloon catheters are commonly used in angioplasty procedures to dilate blood vessels which have become occluded by sclerotic deposits. They comprise a hollow inner and outer shaft with an inflatable balloon located near the patient or distal end of the catheter. The catheter is inserted by sliding it along a guide wire extending through the inner shaft until the balloon of the catheter reaches the location of the occlusion. The balloon is then inflated via an inflation housing at the proximal, machine end of the catheter in order to effect the desired dilatation of the blood vessel. When the procedure is completed, the balloon is deflated and the catheter is removed from the body.

In some catheters, such as described in GB 2130093, the balloon forms a part of the outer shaft. Fluid to expand the balloon is supplied via an annular gap between the inner and outer shafts. In such an arrangement, expansion of the balloon will result in a shortening of the overall length of the outer shaft thereby resulting in a change in the relative lengths of inner and outer shafts. This change in relative length is accommodated in conventional catheters at their machine end by means of a helical spring which allows relative movement between the two shafts and urges the balloon to its unexpanded condition when fluid pressure is removed. A sliding seal within the inflation housing prevents loss of fluid.

This arrangement is relatively complex and expensive and any restriction in this relative movement can compromise the performance of the catheter.

BRIEF SUMMARY OF THE INVENTION

It is an object of the present invention to provide a balloon dilatation catheter that can be used to avoid the above mentioned disadvantages.

According to one aspect of the present invention there is provided a balloon dilatation catheter comprising a flexible inner shaft and an outer shaft embracing the inner shaft, the outer shaft having an expansible balloon portion towards its patient end that is inflatable by means of fluid introduced to the catheter to produce dilatation of the vessel within which the catheter is located, the outer shaft and inner shaft being fixed relative to one another at both ends, such that when the balloon portion is inflated it causes a shortening of the outer shaft, and the flexibility of the inner shaft being such that its excess length on shortening of the outer shaft is accommodated within the balloon portion by bending of the inner shaft within the balloon portion.

According to another aspect of the present invention there is provided a balloon dilatation catheter comprising a flexible inner shaft and an outer shaft embracing the inner shaft, the outer shaft having a balloon portion towards its patient end that is expanded by fluid pressure within the outer shaft, the outer and inner shafts being fixed relative to one another at both ends, and the inner shaft being bent within the balloon portion such that when the balloon portion is deflated by removal of the fluid pressure, the inner shaft within the balloon portion straightens.

The inner shaft is preferably bent into a coil within the balloon portion. An annular passage may be provided between the inner and outer shafts by which fluid can be supplied to or from the balloon portion. The balloon portion is preferably resilient. The inner shaft may be hollow along its length such that a guide wire can be inserted through the catheter. The outer shaft may include a braided sleeve extending along the major part at least of the length of the outer shaft which may have a pick rate in the balloon portion that is different from that in the remainder of the outer shaft such that the braided sleeve is more expansible in the balloon portion than in the remainder of the outer shaft.

A coronary balloon dilatation catheter in accordance with the present invention, will now be described, by way of example, with reference to the accompanying drawings.

BRIEF DESCRIPTION OF THE DRAWINGS

FIG. 1 is a side elevation view of the catheter;

FIG. 2 is a partly sectional side elevation view of the proximal end of the catheter to a larger scale;

FIG. 3 is a sectional side elevation view to a larger scale of the part indicated by the line III in FIG. 1; and FIGS. 4A and 4B show the patient end of the catheter in different conditions.

DETAILED DESCRIPTION OF THE PREFERRED EMBODIMENT

With reference to FIG. 1, the catheter has an inflatable balloon 1 close to its distal or patient end 2 which is inflated by means of fluid introduced to the proximal end 3 of the catheter via an inflation housing 4. When uninflated, the balloon 1 has the same diameter as the remainder of the catheter shaft.

With reference now also to FIGS. 2 and 3, the catheter includes an inner shaft 10 and an outer shaft 20 which is fixed relative to the inner shaft at both its patient end 2 and proximal end 3. The inner shaft 10 is hollow and is of a flexible plastics material, such as a nylon, PVC or polyurethane extrusion. The proximal end of the inner shaft 10 is secured and sealed by means of an adhesive into the inflation housing 4.

The inflation housing 4 has a central bore 40 which is stepped to a reduced diameter passage 41 in which the proximal end of the inner shaft 10 is secured. This opens within an axial port 42 to a larger diameter, female luer taper 43. The port 42 is provided at its proximal end with a locking screw 44. The forward end of the central bore 40 also communicates with an inclined side bore 45 that extends through a side port 46. The side port 46 is similarly provided with a female luer taper and a locking screw 47. The inflation housing 4 is moulded in two parts from a rigid or semi-rigid plastics such as ABS. The axial port 42 is a separately moulded component which is subsequently bonded into a recess 48 in the main part of the housing 4.

The outer shaft 20 has an internal diameter slightly greater than the external diameter of the inner shaft 10, so that there is an annular fluid passage along the catheter between the inner and the outer shafts. The inner surface of the outer shaft 20, or the outer surface of the inner shaft 10 may be coated with a layer of lubricant such as a hydrophilic material (not shown). The outer shaft 20 comprises a combination of layers of rigid and flexible polyurethanes. The first, inner layer 21 comprises a single coat of a rigid polyurethane in all but the region of the balloon 1. This is followed by a second layer 22 comprising a flexible, elastic polyurethane. Around the second layer 22 there is braided a fabric layer 23 of a polyester floss. The braided layer 23 extends the entire length of the outer shaft 20 but varies in pick rate in the manner described in GB 2130093. More particularly, the braiding is more open, that is, it has a lower pick rate in the region of the balloon 1 than over the remainder of the outer shaft. The braided layer 23 is encapsulated by a further layer 24 of flexible, elastic polyurethane. This layer 24 is thicker in the region of the balloon 1. The remainder of the outer shaft is coated with rigid polyurethane 25. In this way, the construction of the outer shaft 20 in the region of the balloon 1 is such that this region is resilient and expansible radially by internal fluid pressure, whereas the remainder of the outer shaft is relatively inexpansible. The extent of expansion of the balloon is limited by the braided layer 23.

Two radio-opaque markers 26 and 27 are located at opposite ends of the balloon 1. The proximal marker 26 lies within the thickness of the shaft 20, between the layers 22 and 23, and comprises a metal foil, such as gold or platinum; the distal marker 27 is a stainless steel or nickel silver ring located within the annular space between the inner shaft 10 and the outer shaft 20.

At its patient, distal end, the outer shaft 20 is bonded to the inner shaft 10 with adhesive in the region of the marker 27 and by moulding the inner shaft into a tapered shape to form the tip of the catheter, as shown in FIGS. 4A and 4B.

At its proximal end, the outer shaft 20 is encompassed by a short collar 29 of a heat shrink material and is secured by means of an adhesive or solvent weld to the inflation housing 4. More particularly, the outer shaft 20 terminates forwardly of the inner shaft 10 and is sealed into the forward part of the central bore 40 so that it communicates with the side port 46 by which fluid can be supplied to inflate the balloon 1.

In operation, a flexible guide wire 50 is inserted into the coronary artery to the location of the occlusion using conventional radiographic techniques. The proximal end of the guide wire 50 is then inserted through the patient end of the catheter, as shown in FIG. 4A, along the bore of the inner shaft 10, and out of the bore 43 through the inflation housing 4. The catheter is pushed along the guide wire 50 until the balloon 1 is located at the site of the occulsion. A measured quantity of sterile liquid is then injected through the side port 46 to dilate the balloon 1, as shown in FIG. 4B, and thereby dilate the occluded blood vessel.

The operation of inflating the balloon 1 causes a a reduction in the length of the outer sleeve 20 and hence of the catheter. This causes an axial compression force to be exerted on the inner shaft 10 because this is fixed to the outer sleeve 20 at both ends. The change in length of the catheter is accommodated by bending of the inner shaft 10 within the balloon, as shown in FIG. 4B. More particularly, the inner shaft 10 coils into a spiral 100 along that part of its length within the balloon 1 but, because of the smaller clearance between the inner shaft and the inner surface of the outer shaft 20 along the remainder of the catheter, it remains coaxial with the outer shaft proximal of the balloon. The flexibility of the inner shaft 10 is selected so that it is flexible enough to prevent kinking but not so flexible that it will fold.

The resilience of the inner shaft 10 acts as a spring to exert an axial force tending to lengthen the outer shaft 20. This, together with the resilience of the balloon 1 itself and the presence of the guide wire, restores the balloon to its uninflated state when fluid pressure is removed, and allows the shaft 10 to straighten.

The arrangement of the present invention considerably simplifies the construction of the inflation housing at the proximal end of the catheter because there are no moving components. Fluid-tight seals can be produced easily because there is no need to make a seal to sliding components.

These advantages are particularly useful with small diameter catheters such as used in coronary dilatation. Similar catheters can, however, be used for dilatation of larger, peripheral blood or other vessels.

What we claim is:

1. In a balloon dilatation catheter of the kind comprising a flexible inner shaft and an outer shaft embracing the inner shaft, the outer shaft having an expansible balloon portion towards its patient end that is inflatable by means of fluid introduced to the catheter to produce dilatation of a vessel within which the catheter is located, the improvement wherein the outer and inner shafts are fixed relative to one another at both ends, such that when the balloon portion is inflated it causes a shortening of the outer shaft, and wherein the flexibility of the inner shaft is such that its excess length on shortening of the outer shaft is accommodated within the balloon portion by bending of the inner shaft within the balloon portion.

2. A catheter according to claim 1, wherein the inner shaft is bent into a coil within the balloon portion.

3. A catheter according to claim 1, wherein the catheter has an annular passage between the inner and outer shafts and an inflation housing towards the machine end of the catheter which communicates with the annular passage such that fluid can be supplied to or from the balloon portion via the inflation housing and the annular passage.

4. A catheter according to claim 1, wherein the balloon portion is resilient.

5. A catheter according to claim 1, wherein the inner shaft is hollow along its length such that a guide wire can be inserted through said catheter.

6. A catheter according to claim 1, wherein the outer shaft includes a braided sleeve extending along the major part at least of the length of the outer shaft.

7. A catheter according to claim 6, wherein the braided sleeve has a pick rate in the balloon portion that is different from that in the remainder of the outer shaft such that the braided sleeve is more expansible in the balloon portion than in the remainder of the outer shaft.

8. In a balloon dilatation catheter of the kind comprising a flexible inner shaft and an outer shaft embracing the inner shaft, the outer shaft having a balloon portion towards its patient end that is expanded by fluid pressure within the outer shaft, the improvement wherein the outer and inner shafts are fixed relative to one another at both ends, and wherein the inner shaft is bent within the balloon portion such that when the balloon portion is deflated by removal of the fluid pressure, the inner shaft within the balloon portion straightens.

9. A catheter according to claim 8, wherein the inner shaft is bent into a coil within the balloon portion before removal of the fluid pressure.

10. A catheter according to claim 8, wherein the balloon portion is resilient.

* * * * *